(12) United States Patent
Axelrod et al.

(10) Patent No.: US 7,897,145 B2
(45) Date of Patent: Mar. 1, 2011

(54) METHODS FOR THE TREATMENT OF RENAL FAILURE

(75) Inventors: Jonathan Axelrod, Jerusalem (IL); Daniel Barkan, Tel Aviv (IL); Eithan Galun, Har Adar (IL); Yael Nehemia, Jerusalem (IL); Stefan Rose-John, Schelhorn (DE)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 257 days.

(21) Appl. No.: 11/916,773

(22) PCT Filed: Jun. 15, 2006

(86) PCT No.: PCT/IL2006/000698
§ 371 (c)(1), (2), (4) Date: Jul. 1, 2008

(87) PCT Pub. No.: WO2006/134601
PCT Pub. Date: Dec. 21, 2006

(65) Prior Publication Data
US 2010/0135952 A1 Jun. 3, 2010

Related U.S. Application Data

(60) Provisional application No. 60/690,869, filed on Jun. 16, 2005.

(51) Int. Cl.
*A61K 45/00* (2006.01)
*A61K 38/00* (2006.01)
*A01N 37/18* (2006.01)

(52) U.S. Cl. .......................... 424/85.2; 514/1.1

(58) Field of Classification Search .................. None
See application file for complete search history.

(56) References Cited

U.S. PATENT DOCUMENTS
5,919,763 A 7/1999 Galun et al.

FOREIGN PATENT DOCUMENTS

| WO | WO 97/32891 | 9/1997 |
|---|---|---|
| WO | WO 99/62534 | 12/1999 |
| WO | WO 01/54706 | 8/2001 |
| WO | WO 03/029281 | 4/2003 |
| WO | WO 2005/113591 | 5/2005 |

OTHER PUBLICATIONS

Saito M., et al. J. Immunol. 148(12):4066-4071, 1992.*
Database WPI Week 199407 Derwent Publications Ltd., London, GB; AN 1994-053923 & JP 06009427 abstract.
Yoshino J. et al., "Leukemia inhibitory factor is involved in tubular regeneration after experimental acute renal failure". J Am Soc Nephrol. Dec. 2003;14(12):3090-101.
Feinglass S. et al., "Treatment of lupus-induced thrombocytopenia with recombinant human interleukin-11". Arthritis Rheum. Jan. 2001;44(1):170-5.
Reznikov L. et al., "Suppression of endotoxin-inducible cytokines in whole blood from human subjects following single dose of recombinant human interleukin-II". Journal of Endotoxin Research 1999 5:197-204.
Fischer M. et al., "I. A bioactive designer cytokine for human hematopoietic progenitor cell expansion". Nat Biotechnol. Feb. 1997;15(2):142-5.
Peters M. et al., "In vivo and in vitro activities of the gp130-stimulating designer cytokine Hyper-IL-6". J Immunol. Oct. 1, 1998;161(7):3575-81.
Homsi E. et al., "Interleukin-6 stimulates tubular regeneration in rats with glycerol-induced acute renal failure". Nephron. Sep. 2002;92(1):192-9.
Wang YD. et al., "gp130-linked signal transduction promotes the differentiation and maturation of dendritic cells". Int Immunol. Jun. 2002;14(6):599-603.
Berns KI. et al., "Adenovirus and adeno-associated virus as vectors for gene therapy". Ann N Y Acad Sci. Nov. 27, 1995;772:95-104.
Fink DJ. et al., "Gene transfer to neurons using herpes simplex virus-based vectors". Annu Rev Neurosci. 1996;19:265-87.
Federoff HJ. et al., "Expression of nerve growth factor in vivo from a defective herpes simplex virus I vector prevents effects of axotomy on sympathetic ganglia". Proc Natl Acad Sci U S A. Mar. 1, 1992;89(5):1636-40.
Liu F. et al., "Hydrodynamics-based transfection in animals by systemic administration of plasmid DNA". Gene Ther. Jul. 1999;6(7):1258-66.
Lemay S. et al., "Prominent and sustained up-regulation of gp130-signaling cytokines and the chemokine MIP-2 in murine renal ischemia-reperfusion injury". Transplantation. Mar. 15, 2000;69(5):959-63.

* cited by examiner

*Primary Examiner* — Robert Landsman
(74) *Attorney, Agent, or Firm* — Winston & Strawn LLP

(57) ABSTRACT

The present invention relates to methods for treating renal failure. Particularly, the present invention relates to methods for treating renal failure by administering to a subject complexes that include a member of the IL-6 family linked to a soluble receptor of the member of the IL-6 family, or isolated polynucleotides encoding same, the complexes capable of activating a gp130 mediated signaling pathway, thereby treating acute or chronic renal failure.

7 Claims, 5 Drawing Sheets

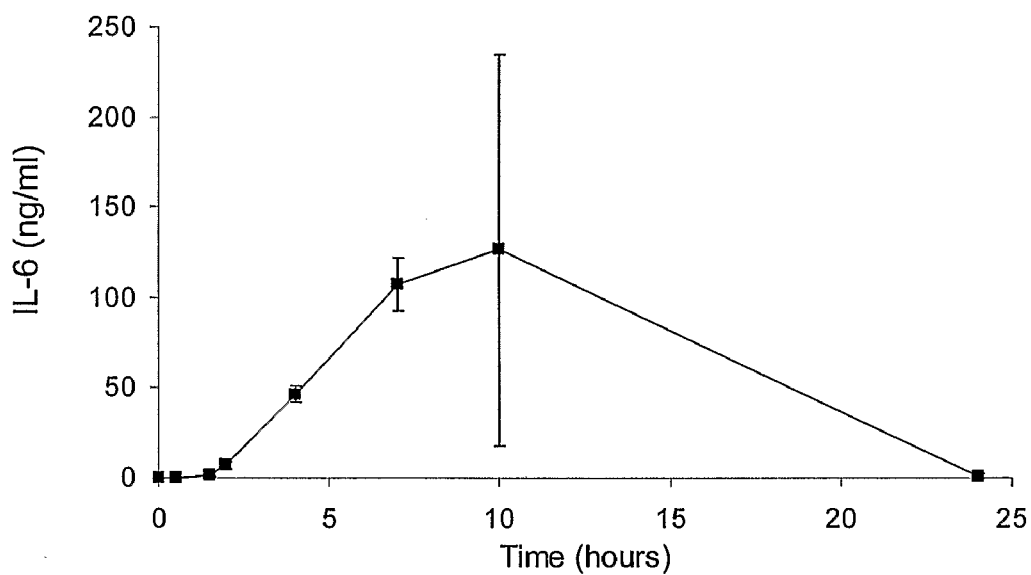
FIG. 1A
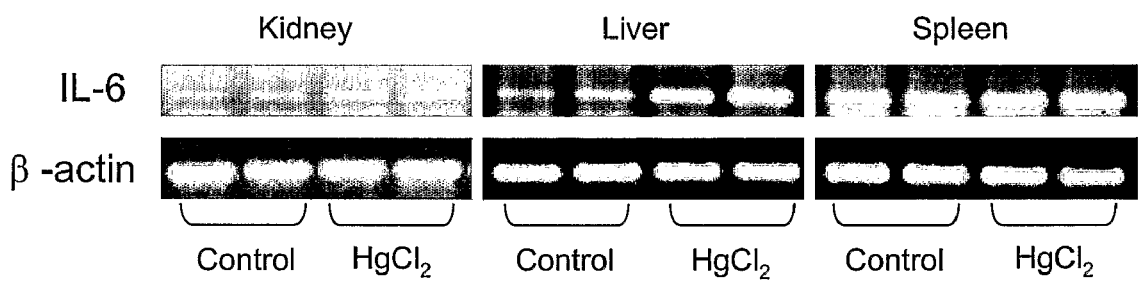
FIG. 1B
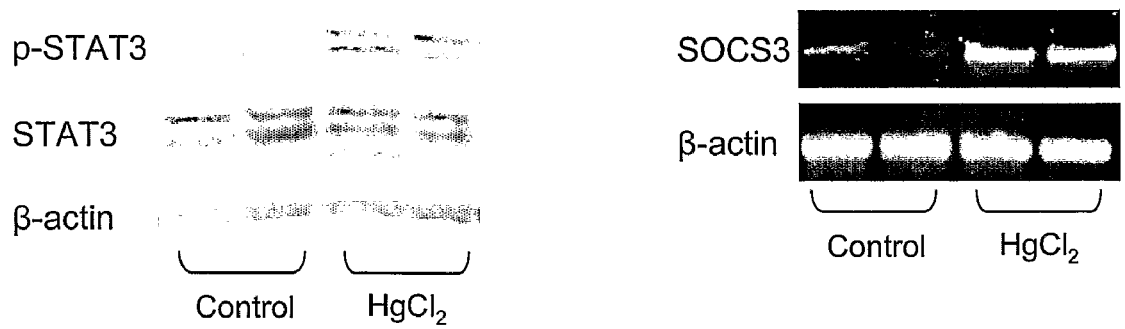
FIG. 1C
FIG. 1D

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: Synthetic sequence

<400> SEQUENCE: 1
aaggagttca cggtgttgct                                              20

<210> SEQ ID NO 2
<211> LENGTH: 20
<212> TYPE: DNA
<213> ORGANISM: Artificial
<220> FEATURE:
<223> OTHER INFORMATION: Synthetic sequence

<400> SEQUENCE: 2
tcgtactgat cctcgtggtt                                              20
```

```
<210> SEQ ID NO 3
<211> LENGTH: 20
<212> TYPE: DNA
<213> ORGANISM: Artificial
<220> FEATURE:
<223> OTHER INFORMATION: Synthetic sequence

<400> SEQUENCE: 3
aaggtgacag cattgcttct                                                 20

<210> SEQ ID NO 4
<211> LENGTH: 18
<212> TYPE: DNA
<213> ORGANISM: Artificial
<220> FEATURE:
<223> OTHER INFORMATION: Synthetic sequence

<400> SEQUENCE: 4
ggctgcctca acacctca                                                   18

<210> SEQ ID NO 5
<211> LENGTH: 20
<212> TYPE: DNA
<213> ORGANISM: Artificial
<220> FEATURE:
<223> OTHER INFORMATION: Synthetic sequence

<400> SEQUENCE: 5
ggtgagtcgg attgcaagtt                                                 20

<210> SEQ ID NO 6
<211> LENGTH: 20
<212> TYPE: DNA
<213> ORGANISM: Artificial
<220> FEATURE:
<223> OTHER INFORMATION: Synthetic sequence

<400> SEQUENCE: 6
gaggtgagtg gacggtcagt                                                 20

<210> SEQ ID NO 7
<211> LENGTH: 20
<212> TYPE: DNA
<213> ORGANISM: Artificial
<220> FEATURE:
<223> OTHER INFORMATION: Synthetic sequence

<400> SEQUENCE: 7
tcagtaccag cggaatcttc                                                 20

<210> SEQ ID NO 8
<211> LENGTH: 22
<212> TYPE: DNA
<213> ORGANISM: Artificial
<220> FEATURE:
<223> OTHER INFORMATION: Synthetic sequence

<400> SEQUENCE: 8
tactgatcca ggaatctccc ga                                              22

<210> SEQ ID NO 9
<211> LENGTH: 20
<212> TYPE: DNA
<213> ORGANISM: Artificial
<220> FEATURE:
<223> OTHER INFORMATION: Synthetic sequence
```

```
<400> SEQUENCE: 9
atacaaccag tgagtggagc                                                20

<210> SEQ ID NO 10
<211> LENGTH: 20
<212> TYPE: DNA
<213> ORGANISM: Artificial
<220> FEATURE:
<223> OTHER INFORMATION: Synthetic sequence

<400> SEQUENCE: 10
gtacaaggaa gccatcacca                                                20

<210> SEQ ID NO 11
<211> LENGTH: 20
<212> TYPE: DNA
<213> ORGANISM: Artificial
<220> FEATURE:
<223> OTHER INFORMATION: Synthetic sequence

<400> SEQUENCE: 11
ctgtacgagg accctccaga                                                20

<210> SEQ ID NO 12
<211> LENGTH: 20
<212> TYPE: DNA
<213> ORGANISM: Artificial
<220> FEATURE:
<223> OTHER INFORMATION: Synthetic sequence

<400> SEQUENCE: 12
tctttgtctg acggagctga                                                20

<210> SEQ ID NO 13
<211> LENGTH: 20
<212> TYPE: DNA
<213> ORGANISM: Artificial
<220> FEATURE:
<223> OTHER INFORMATION: Synthetic sequence

<400> SEQUENCE: 13
catgctttca ggctttcctc                                                20

<210> SEQ ID NO 14
<211> LENGTH: 20
<212> TYPE: DNA
<213> ORGANISM: Artificial
<220> FEATURE:
<223> OTHER INFORMATION: Synthetic sequence

<400> SEQUENCE: 14
tctctgcttc cacccagact                                                20
```

METHODS FOR THE TREATMENT OF RENAL FAILURE

This application is a 371 filing of International Patent Application PCT/IL2006/000698 filed Jun. 15, 2006, which claims the benefit of U.S. provisional application No. 60/690,869 filed Jun. 16, 2005, the contents of each of which is expressly incorporated in its entirety by reference herein.

FIELD OF THE INVENTION

The present invention relates to methods for preventing or treating renal failure. Particularly, the present invention relates to methods for preventing or treating renal failure comprising administering to a subject complexes comprising a member of the IL-6 family linked to a soluble receptor of the member of the IL-6 family, or isolated polynucleotides encoding same, the complexes capable of activating a gp130 mediated signaling pathway, thereby preventing or treating acute or chronic renal failure.

BACKGROUND OF THE INVENTION

Acute renal failure (ARF) remains a major source of morbidity and mortality in hospitalized patients, complicating the course of 5-7% of hospital admissions and up to 30% of intensive care units admissions. Approximately 40% of ARF cases are defined as acute tubular necrosis (ATN). ATN is also the final common pathway in severe renal dysfunction in patients suffering from diseases of non-renal origin (so-called pre and post renal failure).

Interleukin-6 (IL-6) is a member of a family of cytokines, including leukemia inhibitory factor (LIF), cardiotrophin-1 (CT-1), ciliary neurotrophic factor (CNTF), IL-11, and oncostatin M (OSM), which acts via receptor complexes that contain at least one subunit of the ubiquitously expressed signal transducing protein, gp130.

On target cells, IL-6 acts by binding to a specific cognate receptor designated interleukin-6 receptor (IL-6R), which triggers gp130 and leads to the activation of the Janus kinase (Jak)/signal transduction and activator of transcription (STAT) signaling pathway, and in particular the activation of STAT-3. Unlike the ubiquitously expressed gp130, the cellular distribution of IL-6R is limited to a few cell types including hepatocytes, and some leukocyte sub-populations including monocytes, neutrophils, and some T cells and B cells. However, the IL-6R also exists in a soluble form (sIL-6R), which together with IL-6 generates a complex that stimulates cells via direct interaction with gp130. Importantly, in a process called IL-6 trans-signaling, IL-6/sIL-6R complexes act as an agonist on cell types that, although they express gp130, would not inherently respond to IL-6 alone.

A recombinant fusion protein called Hyper-IL-6 consisting of human IL-6 linked by a flexible peptide chain to sIL-6R was shown to be a super agonistic designer cytokine (Fischer, M., et al. Nat. Biotechnol. 15: 142-145, 1997). Hyper-IL-6 was found to be more active than the combination of unlinked IL-6 and sIL-6R on gp130-expressing cells, and to exhibit a super agonistic effect both in vitro and in vivo (Peters, M., et al. J. Immunol. 161: 3575-3581, 1998).

U.S. Pat. No. 5,919,763 to Galun et al. discloses methods for treating an injury to a liver of a subject comprising administering to the subject a pharmaceutical composition comprising an IL-6/sIL-6R complex, preferably Hyper-IL-6.

International Application Publication No. WO 99/62534 of Galun et al. discloses methods for treating an injury to a liver of a subject comprising administering to the subject a pharmaceutical composition comprising an IL-6/sIL-6R complex, preferably Hyper-IL-6. WO 99/62534 further discloses methods of gene therapy for treating an injury to a liver of a subject comprising administering to the subject a vector carrying Hyper-IL-6 chimera gene.

International Application Publication No. WO 03/029281 of Axelrod et al. discloses a therapeutic composition comprising an IL-6 family combination component and a liver regenerating factor, preferably the IL-6 family combination component is a IL-6/sIL-6 complex. WO 03/029281 further discloses methods for treating a pathological condition in a subject comprising administering to the subject a therapeutic composition comprising an IL-6 family combination component and a liver regenerating factor, wherein at least one of the IL-6 family combination component and the liver regenerating factor is administered encoded by a plasmid. Among the pathological conditions listed, kidney disease including renal failure is indicated.

Leukemia Inhibitory Factor (LIF) and LIF receptor mRNA expression was shown to be increased significantly during the recovery phase after acute renal failure (Yoshino, J., et al., J. Am. Soc. Nephrol. 14: 3090-3101, 2003). The increased expression of LIF mRNA and protein was pronounced mostly in the S3 segment of the proximal tubules. It was suggested that LIF is involved in tubular regeneration after experimental acute renal failure (Yoshino, T., et al. ibid). However, no specific enablement or guidance is provided for inducing renal regeneration by LIF only or LIF-soluble LIF receptor complex after ARF.

International Application Publication No. WO 2005/113591 discloses a fusion polypeptide consisting of soluble IL-11 receptor (sIL-11R) and IL-11 and uses thereof for the treatment of a proliferative disease, a cytopathy, radiation damage, an IL-11 dependent inflammatory disorder, IL-11 dependent degenerative disorders, and IL-11 dependent or mediated soft tissue disorders.

IL-6 was shown to stimulate tubular regeneration in rats with glycerol-induced ARF (Homsi, E., et al., Nephron 92: 192-199, 2002). IL-6 administered to these rats caused a significant increase in tubular cell proliferation in the cortex and medulla, however it failed to accelerate recovery of renal function in the rats (Homsi, E., et al., ibid).

It would be highly advantageous to have improved methods for the treatment or prevention of renal failure which maintain or restore renal function and thereby reduce mortality caused by renal failure.

SUMMARY OF THE INVENTION

The present invention provides new methods for treating or preventing renal failure in a subject comprising administering to the subject in need thereof a pharmaceutical composition comprising as an active agent at least one polypeptide capable of activating a gp130 mediated signaling pathway. The present invention further provides methods for treating or preventing renal failure comprising administering to a subject in need thereof a pharmaceutical composition comprising as an active agent an isolated polynucleotide encoding at least one polypeptide, the at least one polypeptide capable of activating a gp130 mediated signaling pathway. The present invention further provides methods for treating or preventing renal failure comprising administering to a subject in need thereof a pharmaceutical composition comprising as an active agent an expression vector, the expression vector comprising an isolated polynucleotide encoding at least one polypeptide, the at least one polypeptide capable of activating a gp130 mediated signaling pathway.

It is now disclosed for the first time that IL-6/soluble IL-6 receptor (sIL-6R) complexes, designated herein Hyper-IL-6 or HIL-6, or expression vectors comprising a polynucleotide encoding Hyper-IL-6 are capable of preventing the onset of acute tubular necrosis (ATN) which leads to acute renal failure (ARF). Pretreatment of test animals with Hyper-IL-6 protects the test animals from the development of ARF and thereby prolongs the life span of the treated animals.

It is further disclosed that Hyper-IL-6 can protect renal tubules from necrosis. The protection of renal tubules from necrosis or failure involves a gp130 mediated signaling cascade. Unexpectedly, activation of the gp130 mediated signaling cascade and preventing ARF can be achieved not only by administering a cytokine/soluble cytokine receptor complex polypeptide such as Hyper-IL-6, but also by administering a plasmid comprising an isolated polynucleotide encoding the cytokine/soluble cytokine receptor complex such as Hyper-IL-6. Surprisingly, systemic administration of the plasmid is highly efficient in achieving the protective or preventive effect of the cytokine/soluble cytokine receptor complex such as Hyper-IL-6. Thus, the methods of the present invention are highly useful for preventing tubular necrosis and ARF, for protecting against renal failure, and for overall maintenance of renal function.

According to one aspect, the present invention provides a method for preventing or treating renal failure in a subject comprising administering to the subject a pharmaceutical composition comprising as an active agent at least one polypeptide capable of activating a gp130 mediated signaling pathway and a pharmaceutically acceptable carrier, thereby treating or preventing the renal failure.

According to some embodiments, the at least one polypeptide within the pharmaceutical composition is a member of the IL-6 family selected from the group consisting of IL-11, leukemia inhibitory factor (LIF), oncostatin M (OSM), ciliary neurotrophic factor (CNTF), cardiotrophin-1 (CT-1), cardiotrophin-like cytokine (CTC), and biologically active fragments, variants and salts thereof.

According to further embodiments, the at least one polypeptide is a complex comprising a member of the IL-6 family linked to a soluble receptor of the member of the IL-6 family. According to some embodiments, the pharmaceutical composition to be administered to the subject comprises as an active agent said complex excluding exogenous liver regenerating factors. According to additional embodiments, the pharmaceutical composition to be administered to the subject comprises as an active agent said complex excluding exogenous growth factors. According to additional embodiments, the pharmaceutical composition to be administered to the subject comprises as an active agent said complex excluding exogenous immunoglobulins or fragments thereof.

According to additional embodiments, the complex is selected from the group consisting of IL-6/soluble IL-6 receptor (sIL-6R) complex, IL-11/soluble IL-11 receptor (sIL-11R) complex, LIF/soluble LIF receptor (sLIFR) complex, OSM/soluble OSM receptor (sOSMR) complex, CNTF/soluble CNTF receptor (sCNTFR) complex, CT-1/soluble CT-1 receptor (sCT-1R) complex, CTC/soluble CTC receptor (sCTCR) complex, and biologically active fragments, variants and salts thereof. According to one embodiment, the complex is IL-6/sIL-6R complex, preferably Hyper-IL-6. According to another embodiment, the complex is IL-11/sIL-11R. According to a further embodiment, the complex is LIF/sLIFR. According to a still further embodiment, the complex is OSM/sOSMR. According to yet further embodiment, the complex is CNTF/sCNTFR. According to another embodiment, the complex is CT-1/sCT-1R. According to a further embodiment, the complex is CTC/sCTCR.

According to other embodiments, the at least one polypeptide capable of activating a gp130 mediated signaling pathway is selected from the group consisting of monoclonal antibodies directed to gp130, polyclonal antibodies directed to gp130, and small synthetic molecules capable of activating a gp130 mediated signaling pathway.

According to another aspect, the present invention provides a method for preventing or treating renal failure in a subject comprising administering to the subject a pharmaceutical composition comprising as an active agent an isolated polynucleotide encoding at least one polypeptide according to the principles of the present invention and a pharmaceutically acceptable carrier, wherein the at least one polypeptide capable of activating a gp130 mediated signaling pathway, thereby preventing or treating renal failure.

According to still a further aspect, the present invention provides a method for preventing or treating renal failure in a subject comprising administering to the subject a pharmaceutical composition comprising as an active agent an expression vector comprising an isolated polynucleotide encoding at least one polypeptide according to the principles of the present invention, and a pharmaceutically acceptable carrier, wherein the polypeptide capable of activating a gp130 mediated signaling pathway, thereby preventing or treating renal failure.

According to some embodiments, the expression vector is selected from the group consisting of naked DNA or RNA molecules, plasmids and viral vectors.

According to yet another aspect, the present invention provides a method for preventing or treating renal failure in a subject comprising administering to the subject a pharmaceutical composition comprising as an active agent a host cell transfected with an expression vector, the expression vector comprising an isolated polynucleotide encoding at least one polypeptide according to the principles of the present invention, and a pharmaceutically acceptable carrier, wherein the polypeptide capable of activating a gp130 mediated signaling pathway, thereby preventing or treating renal failure.

According to additional embodiments, the renal failure to be treated with any of the pharmaceutical compositions of the present invention is selected from the group consisting of acute renal failure, chronic renal failure, and end stage renal disease. According to a currently exemplary embodiment, the renal failure to be treated with any of the pharmaceutical compositions of the present invention is acute renal failure.

Acute renal failure to be treated can arise from use or exposure of a subject to a pharmaceutical agent, diagnostic agent or toxic agent selected from the group consisting of antibiotics, antifungal agents, radio-contrast agents, imaging agents, chemotherapeutic agents, metals, organic solvents, and carbon tetrachloride.

According to further embodiments, the acute renal failure to be treated with any of the pharmaceutical compositions of the present invention can arise for a disease, disorder or condition selected from the group consisting of myoglobinuric rhabdomyolysis, hemoglobinuria, atheroembolic disease, renal artery occlusion, vasculitis, hemolytic-uremic syndrome, thrombolytic thrombocytopenic purpura, Wegener's granulomatosis, systemic lupus erythematosus, Henoch-Schoenlein purpura, Goodpasture's syndrome, acute glomerulonephritis, acute hypersensitivity interstitial nephritis, hypercalcemia, urinary tract obstruction, acute uric acid nephropathy, pyelonephritis, papillary necrosis, hepatorenal syndrome, hypertension, bacterial sepsis, systemic inflammatory shock, fungemia, acute viral disease, severe volume depletion, burns, surgical procedures, ischemia-reperfusion, and post-partum complications.

According to yet further embodiments, chronic renal failure includes, but is not limited to, chronic diabetic nephropathy, diabetic glomerulopathy, diabetic renal hypertrophy, hypertensive nephrosclerosis, hypertensive glomerulosclerosis, renal dysplasia, glomerular hypertrophy, tubular hypertrophy, glomerulosclerosis and tubulointerstitial sclerosis.

According to some embodiments, the route of administering any of the pharmaceutical compositions of the present invention is selected from the group consisting of topical, intradermal, intramuscular, intraperitoneal, intravenous, subcutaneous, intranasal, and oral administration routes. According to an exemplary embodiment, administering the pharmaceutical composition of the invention is via intravenous administration.

These and other embodiments of the present invention will be better understood in relation to the figures, description, examples and claims that follow.

BRIEF DESCRIPTION OF THE FIGURES

FIGS. 1A-D show the expression of IL-6 after $HgCl_2$ treatment. FIG. 1A shows IL-6 levels in serum samples obtained from mice treated with $HgCl_2$. Results are expressed as mean±SEM. FIG. 1B shows RT-PCR analysis of IL-6 mRNA in liver, kidney and spleen tissue samples taken from mice 6 hours after treatment with $HgCl_2$. FIG. 1C shows Western blot analysis of phosphorylated STAT3 (p-STAT; Tyr 705) and STAT3 in the kidney prior to and after $HgCl_2$ induced injury. FIG. 1D shows RT-PCR analysis of SOCS3 mRNA induction after $HgCl_2$ induced injury.

FIG. 2A shows that pre-treatment with exogenous human IL-6 protein (20 μg, i.v.) fails to protect mice from $HgCl_2$ induced ARF as indicated by BUN levels measured in the mice. Control mice were injected with saline only 4 hours prior to administration of $HgCl_2$. Results are expressed as mean±SEM of surviving mice. FIG. 2B shows Kaplan-Meier plot of survival in mice of FIG. 2A. FIG. 2C, Western blot analysis of IL-6R from normal murine liver and kidney. The blots were stripped and re-probed for β-actin protein as a control. FIG. 2D, IL-6R mRNA analysis by RT-PCR of RNA extracts from normal liver, normal kidney, and kidney tissue 6 hours post $HgCl_2$ administration. RT-PCR analysis of β-actin mRNA is shown for comparison.

FIG. 3A, Western blot analysis of p-STAT3 (Tyr 705) and STAT3 in the kidney after treatment with PBS, IL-6 (20 μg), or HIL-6 (4 μg). FIG. 3B, Renal function in mice treated with HIL-6 or normal saline 4 hours prior to administration of $HgCl_2$. Results are expressed as mean±SEM. *P<0.002 and **P<0.005. FIG. 3C, Kaplan-Meier survival plot of mice of FIG. 3B. FIG. 3D, Histological changes 24 hours after administration of $HgCl_2$ in mice pre-treated with normal saline or HIL-6 (8 μg, i.v.) 4 hours prior to $HgCl_2$ administration. H&E staining of paraffin embedded kidney sections. Saline pre-treated mice show massive necrosis of tubular epithelial cells (black arrows), dilation of the tubular lumina with accumulation of proteinaceous material (asterisk), and accumulation of neutrophils in the peritubular capillaries (arrowhead). HIL-6 pre-treated mice display subtle tubular injury with occasional apoptotic tubular epithelial cells (arrowhead). Original magnification, ×200 and ×400 (high power field, inset).

FIG. 4A, RT-PCR analysis of kidney mRNAs. FIG. 4B, Western blot analysis of anti-apoptotic factors. Kidneys were collected from mice 4 hours after treatment with IL-6 (20 μg, i.v.) or HIL-6 (8 μg, i.v.), or 6 hours after administration of $HgCl_2$ (6 mg/kg) in mice with or without 4 hours pre-treatment with HIL-6.

DETAILED DESCRIPTION OF THE INVENTION

Figure 2A:
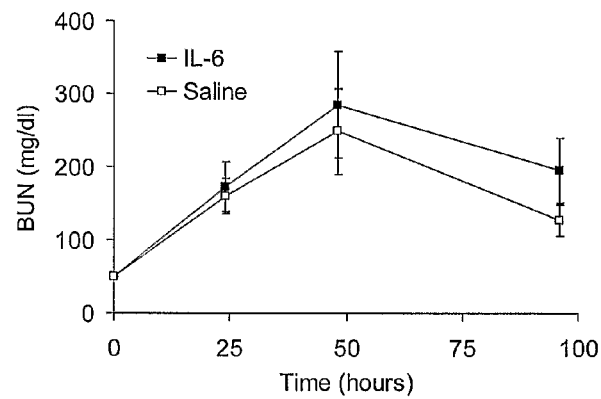
FIGS. 2A-D show the absence of IL-6R expression in murine kidney.

Acute renal failure is defined as an abrupt cessation or substantial reduction of renal function and, in as many as 90-95% of cases, may be secondary to trauma, surgery or another acute medical condition. Acute renal failure may be due to pre-renal causes (e.g., decreased cardiac output, hypovolemia, altered vascular resistance) or to post-renal causes (e.g., obstructions or constrictions of the ureters, bladder or urethra) which do not directly involve the kidneys and which, if treated quickly, will not entail significant loss of nephrons or other damage to the kidneys. Alternatively, acute renal failure may be due to intrinsic renal causes which involve a more direct insult or injury to the kidneys, and which may entail permanent damage to the nephrons or other kidney structures. Intrinsic causes of acute renal failure include, but are not limited to, infectious diseases (e.g., various bacterial, viral or parasitic infections), inflammatory diseases (e.g., glomerulonephritis, systemic lupus erythematosus), ischemia (e.g., renal artery occlusion), toxic syndromes (e.g., heavy metal poisoning, side-effects of antimicrobial treatments or chemotherapy), and direct traumas.

Chronic renal failure may be defined as a progressive, permanent and significant reduction of the glomerular filtration rate (GFR) due to a significant and continuing loss of nephrons. Chronic renal failure typically begins from a point at which a chronic renal insufficiency (i.e., a permanent decrease in renal function of at least 50-60%) has resulted from some insult to the renal tissues which has caused a significant loss of nephron units. The initial insult may or may not have been associated with an episode of acute renal failure. Irrespective of the nature of the initial insult, chronic renal failure manifests a "final common path" of signs and symptoms as nephrons are progressively lost and GFR progressively declines.

The early stage of chronic renal failure typically begins when GFR has been reduced to approximately one-third of normal (e.g., 30-40 ml/min for an average human adult). As a result of the significant nephron loss, and in an apparent "attempt" to maintain the overall GFR with fewer nephrons, the average single nephron GFR (SNGFR) is increased by adaptations of the remaining nephrons at both the structural and functional level. One structural manifestation of this adaptation, readily detectable by microscopic examination of biopsy samples, is a "compensatory hypertrophy" of both the glomeruli and the tubules of the kidney, a process which literally increases the volume of filtrate which can be produced by each remaining nephron by literal enlargement of the glomeruli and tubules. At the same time, there are functional changes in the remaining nephrons, such as decreased absorption or increased secretion of normally excreted solutes, which may be responses to hormonal or paracrine changes elsewhere in the body (e.g., increasing levels of parathyroid hormone (PTH) in response to changes in serum levels of calcium and phosphate).

These adaptations in early stage chronic renal failure are not successful in completely restoring GFR or other parameters of renal function and, in fact, subject the remaining nephrons to increased risk of loss. For example, the increased SNGFR is associated with mechanical stresses on the glomerulus due to hypertension and hyperperfusion. Proliferative effects are also observed in mesangial, epithelial and endothelial cells, as well as increases in the deposition of collagen and other matrix proteins. Sclerosis of both the glomeruli and tubules is another common symptom of the hypertrophied nephrons and the risk of coagulation in the glomerulus is increased. In particular, these adaptations of the remaining nephrons, by pushing the SNGFR well beyond its normal level, actually decrease the capacity of the remaining nephrons to respond to acute changes in water, solute, or acid loads and, therefore, actually increase the probability of additional nephron loss.

As chronic renal failure progresses, and GFR continues to decline to less than 10% of normal (e.g., 5-10 ml/min), the subject enters end-stage renal disease (ESRD). During this phase, the inability of the remaining nephrons to adequately remove waste products from the blood, while retaining useful products and maintaining fluid and electrolyte balance, leads to a rapid decline in which many organ systems, and particularly the cardiovascular system, may begin to fail. For example, blood urea nitrogen (BUN) and creatinine levels may rise and, at BUN levels of 60-100 mg/dl and serum creatinine levels of 8-12 mg/dl, a uremic syndrome will typically develop in which the kidneys can no longer remove the end products of nitrogen metabolism. At this point, renal failure will rapidly progress to death unless the subject receives renal replacement therapy (i.e., chronic hemodialysis, continuous peritoneal dialysis, or kidney transplantation).

The present invention thus provides methods for preventing or treating renal failure in a subject comprising administering to the subject a pharmaceutical composition comprising as an active agent at least one polypeptide capable of activating a gp130 mediated signaling pathway, thereby treating or preventing renal failure. The present invention encompasses pharmaceutical compositions wherein the active agent is a polynucleotide encoding the at least one polypeptide of the invention, an expression vector comprising the polynucleotide encoding said at least one polypeptide or a host cell transfected with the expression vector of the invention.

According to the present invention, polypeptides capable of activating a gp130 mediated signaling pathway include, but are not limited to, members of the IL-6 family such as, for example, IL-11, leukemia inhibitory factor (LIF), oncostatin-M (OSM), ciliary neurotrophic factor (CNTF), cardiotrophin-1 (CT-1), cardiotrophin-like cytokine (CLC), and analogs, fragments, or salts thereof capable of activating the gp130 mediated signaling pathway. It is to be understood that IL-6 is shown herein not to be useful for the prevention of renal failure (see examples below).

Polypeptides capable of activating a gp130 mediated signaling pathway according to the principles of the present invention also include complexes comprising a member of the IL-6 family linked to a soluble receptor of the member of the IL-6 family. As it is known in the art that complexes of a member of the IL-6 family and the corresponding soluble cytokine receptor are capable of activating a gp130 mediated signaling pathway, the present invention contemplates complexes including, but not limited to, IL-6/soluble IL-6 receptor (sIL-6R), IL-11/sIL-11R, LIF/sLIFR, OSM/sOSMR, CNTF/sCNTFR, CT-1/sCT-1R, CLC/sCLCR, and analogs, fragments or salts thereof capable of activating the gp130 mediated signaling pathway.

The term "gp130 mediated signaling pathway" refers to the formation of a receptor complex comprising gp130 that leads to the activation of intracellular pathways such as, for example the Jak/Stat signaling pathway, particularly of STAT-3, the Ras-MAPK signaling pathway, and the like. Without being bound to any theory, the formation of a receptor complex comprising gp130, whether gp130 is present as a dimer or heterodimer in the receptor complex with a receptor of any member of the IL-6 family, can involve conformational changes of gp130, which lead to the activation of intracellular pathways known in the art.

The term "biological activity" refers to the ability of any polypeptide of the invention to activate a gp130 signaling pathway leading to the activation of intracellular pathways. Thus, the terms "biological activity" and "activation of a gp130 signaling pathway" are interchangeable throughout the present specification.

The principles of the present invention are exemplified herein below by the IL-6/soluble IL-6R polypeptide complex. However, it is explicitly intended that the pharmaceutical compositions of the present invention comprise any polypeptide complex comprising a member of the IL-6 family linked to its corresponding soluble receptor, which complex is capable of activating a gp130 signaling pathway and thereby treat or prevent renal failure.

The term "IL-6/sIL-6R complex" refers both to a bimolecular protein complex which features both the IL-6 protein and the soluble IL-6 receptor (SIL-6R) protein, and to a unimolecular protein which includes IL-6 and sIL-6R, preferably the bioactive portions of IL-6 and sIL-6R, connected with a flexible linker substantially as previously described (see International Patent Application Publications Nos. WO 97/32891; WO 99/62534; WO 03/02981; Fischer, M., et al. Nat. Biotechnol. 15: 142-147, 1997; and Peters, M., J. Immunol. 161: 3575-3581, 1998 incorporated by reference as if fully set forth herein) as well as any biologically active analog or fragment thereof. The accession number for IL-6 is M14584 (GenBank Protein Sequences Database), and for the soluble IL-6 receptors is M57230, M20566, and X12830.

The bimolecular protein complex includes IL-6 and sIL-6R or any other member of the IL-6 family and its corresponding soluble receptor at any order as well as biologically active analogs or fragments thereof. The term "biologically active analog" refers to any homologous polypeptide to a member of the IL-6 family including, but not limited to, IL-6, IL-11, LIF, OSM, CNTF, CT-1, CLC, sCLCR, and to any homologous polypeptide to a soluble receptor of a member of the IL-6 family including, but not limited to, sIL-6R, sIL-11R, sLIFR, sOSMR, sCNTFR, sCT-1R, which homologous polypeptide includes any amino acid substitution, deletion, or addition, while retaining the biological activity of the original polypeptide. For example, a biologically active analog of an IL-6/sIL-6R complex should retain the capability to directly activate the membrane receptor for the IL-6/sIL-6R complex known as gp130 or at least one component of the downstream signaling of gp130. The present invention encompasses fragments of the polypeptides disclosed herein so long as the fragments retain the original biological activity of the polypeptide.

The term "Hyper-IL-6" refers to a unimolecular protein, which includes the bioactive portions of IL-6 and sIL-6R connected with a flexible linker, substantially as described in International Patent Application Publication No. WO 97/32891 referred to as "H-IL-6" in that reference.

The term "linker" relates to linkers of any kind, which are suitable for the binding of any member of the IL-6 family and its corresponding soluble receptor. Examples of such linkers include, but are not limited to, bifunctional, chemical cross-linkers, a disulfide-bridge connecting a first amino acid of a member of the IL-6 family and a second amino acids of the corresponding soluble receptor, and a peptide or polypeptide.

The unimolecular protein can be a fusion polypeptide. For example, polypeptides featuring the bioactive portions of IL-6 and sIL-6R can be fused with each other and the linker can be a disulfide-bridge produced by the two polypeptides. Preferably the linker is a polypeptide, which connects the two other polypeptides with each other. These fusion polypeptides can include, for example, a human sIL-6R-polypeptide, which is an extracellular subunit of the human IL-6R and a human IL-6-polypeptide, whereby the sIL-6R and IL-6 are connected by different polypeptide-linkers with each other. The accession number for IL-6 is M14584 (GenBank Protein Sequences Database), and for the soluble IL-6 receptor is M57230, M20566, and X12830.

According to one preferred embodiment of the invention, the unimolecular protein consists of amino acids 114-323 of the sIL-6R-polypeptide and amino acids 29-212 of human IL-6-polypeptide. A bioactive analog consisting of amino acids 113-323 of the sIL-6R-polypeptide and amino acids 29-212 of the IL-6-polypeptide is also encompassed in the present invention. Other unimolecular complexes, bimolecular complexes, analogs, fragments, and combinations thereof are encompassed in the present invention so long as the complexes, analogs, fragments, and combinations thereof retain the capability to activate gp130 or any component of the down-stream signaling of gp130.

The present invention encompasses the use of monoclonal or polyclonal antibodies directed against gp130 for the prevention or treatment of renal failure. For example, the monoclonal antibody, B-S12, an agonist of gp130, used for the activation of gp130 on dendritic cells (see Wang, Y. D., et al., Int. Immunol. 14:599-603, 2002) can be used for the prevention or treatment of renal failure. Other polyclonal or monoclonal antibodies directed against gp130 as known in the art can be useful for practicing the present invention.

By "peptide" it is meant that the peptide comprises not more than 50 amino acids. By "polypeptide" it is meant that the polypeptide generally comprises more than 50 amino acid residues.

By using "amino acid substitution", it is meant that functionally equivalent amino acid residues are substituted for residues within the sequence resulting in a silent change. For example, one or more amino acid residues within the polypeptide sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, non-conservative substitutions, wherein one amino acid within a polypeptide is substituted with an amino acid of a different polarity or hydrophobicity, are also included within the present invention so long as the polypeptide retains the original biological activity. The invention further encompasses polypeptides having one or more amino acids at the D-isomer configuration and polypeptides having one or more non-natural amino acids.

The present invention encompasses polypeptide analogs of which at least one amino acid has been modified. Modifications of amino acid residues include, but are not limited to, glycosylation, oxidation, permanent phosphorylation, reduction, myristylation, sulfation, acylation, acetylation, ADP-ribosylation, amidation, cyclization, disulfide bond formation, hydroxylation, iodination, methylation, derivatization by protecting/blocking groups, or any other derivatization method known in the art. Such modifications, which do not destroy, but maintain or improve the biological activity of the original polypeptide can occur anywhere along the sequence of the analog including at the peptide backbone, at an amino acid side-chain, or at the amino or carboxyl termini.

Polypeptide members of the IL-6 family, complexes comprising same and their corresponding soluble receptors, analogs and fragments thereof such as, for example, IL-6/sIL-6R complex, can be produced by various methods known in the art, including isolation from natural sources, synthetic production or recombinant production.

The polypeptides of the invention can be isolated from natural sources including, but not limited to, blood and urine. The polypeptides can be produced by synthetic production. Synthetic production of polypeptides is well known in the art and is available commercially from a variety of companies. A polypeptide of the invention such as an IL-6/sIL-6R complex can be synthesized using a standard direct peptide synthesis method (e.g., as summarized in Bodanszky, 1984, Principles of Peptide Synthesis, Springer-Verlag, Heidelberg) such as via solid-phase synthesis (see, e.g., Merrifield, 1963, J. Am. Chem. Soc. 85:2149-2154).

Included within the scope of the invention are chimeric or fusion proteins comprising a member of the IL-6 family, a fragment or analog thereof joined at its amino or carboxy-terminus or at one of the side chains via a peptide bond to an amino acid sequence of its corresponding soluble receptor, a fragment or analog thereof. Such fusion proteins can be made by protein synthesis, e.g., by use of a peptide synthesizer, or by ligating the appropriate nucleic acid sequences encoding the desired amino acid sequences to each other by methods known in the art, in the proper coding frame, and expressing the fusion protein by methods commonly known in the art.

Recombinant production can be achieved by the use of an isolated polynucleotide encoding a desired polypeptide, for example an IL-6/sIL-6R complex, or an analog or fragment thereof, the isolated polynucleotide operably linked to a promoter for the expression of the polynucleotide. Optionally, a regulator of the promoter is added. The construct comprising the polynucleotide encoding the polypeptide or an analog or fragment thereof, the promoter, and optionally the regulator can be placed in a vector, such as a plasmid, virus or phage vector. The vector may be used to transfect or transform a host cell, e.g., a bacterial, yeast, insect, or mammalian cell.

The term "polynucleotide" means a polymer of deoxyribonucleic acid (DNA) or ribonucleic acid (RNA), which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

One who is skilled in the art will appreciate that more than one nucleic acid may encode any given protein in view of the degeneracy of the genetic code and the allowance of exceptions to classical base pairing in the third position of the codon, as given by the so-called "Wobble rules". Moreover, polynucleotides that include more or less nucleotides can result in the same or equivalent proteins. Accordingly, it is intended that the present invention encompasses all polynucleotides that encode the polypeptides of the invention, for example IL-6/sIL-6R, preferably Hyper-IL-6.

The polynucleotides of the present invention can be expressed as a transported protein where the polypeptide is isolated from the medium in which the host cell containing the polynucleotide is grown, or may be expressed as an intracellular protein by deleting the leader or other peptides, in which case the polypeptide is isolated from the host cells. The polypeptide so isolated is then purified by protein purification methods known in the art.

The polypeptides of the invention can be provided to the tissue of interest by transferring to cells an expression vector comprising an isolated polynucleotide encoding the polypeptide of the invention. The cells produce and secrete the polypeptide such that it is suitably provided to cells within renal tubules to prevent or treat ARF.

The expression vectors comprise a promoter. In the context of the present invention, the promoter must be able to drive the expression of the polynucleotide within the cells. Many viral promoters are appropriate for use in such an expression cassette including, but not limited to, retroviral ITRs, LTRs, immediate early viral promoters (IEp; such as herpes virus Iep, e.g., ICP4-IEp and ICPO-IEp and cytomegalovirus (CMV) IEp), late viral promoters, latency-active promoters (LAPs), Rous Sarcoma Virus (RSV) promoters, and Murine Leukemia Virus (MLV) promoters. Other suitable promoters are eukaryotic promoters, which contain enhancer sequences (e.g., the rabbit β-globin regulatory elements), constitutively active promoters (e.g., the β-actin promoter, human $\alpha_1$-antitrypsin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the polypeptide of the invention and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors must be introduced into the cells in a manner such that they are capable of expressing the isolated polynucleotide encoding the polypeptide of the invention contained therein. Any suitable vector can be so employed, many of which are known in the art. Examples of such vectors include naked DNA or RNA vectors (such as oligonucleotides or plasmids), viral vectors such as adeno-associated viral vectors (Berns et al., 1995, Ann. N.Y. Acad. Sci. 772: 95-104), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640), papilloma virus vectors, picornavirus vectors, polyoma virus vectors, retroviral vectors, SV40 viral vectors, vaccinia virus vectors, and other vectors known in the art. In addition to the expression vector of interest, the vector can also include other genetic elements, such as, for example, genes encoding a selectable marker (e.g., n-gal or a marker conferring resistance to a toxin), a pharmacologically active protein, a transcription factor, or other biologically active substance.

Methods for manipulating a vector comprising an isolated polynucleotide are well known in the art (see, e.g., Sambrook et al., 1989, Molecular Cloning: A Laboratory Manual, 2d edition, Cold Spring Harbor Press) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising a polynucleotide encoding a polypeptide of the invention, for example an IL-6/sIL-6R complex, preferably Hyper-IL-6, is introduced into the cells by any means appropriate for the transfer of DNA into cells. Many such methods are well known in the art (Sambrook et al., supra; see also Watson et al., 1992, Recombinant DNA, Chapter 12, 2d edition, Scientific American Books). For eukaryotic cells, vectors may be introduced through the use of, for example, electroporation, transfection such as hydrodynamics-based transfection, infection, DNA coated microprojectiles or protoplast fusion (see, for example, Liu, F. et al., 1999, Gene Ther. 6: 1258-1266).

Cells, into which the polynucleotide has been transferred under the control of an inducible promoter if necessary, can be used as transient transformants. Such cells themselves can then be transferred into a mammal for therapeutic benefit therein. Typically, the cells are transferred to a site in the mammal such that the polypeptide of the invention expressed therein and secreted therefrom contacts renal tubular cells in order to prevent or treat a renal failure. Alternatively, particularly in the case of cells to which the vector has been added in vitro, the cells may first be subjected to several rounds of clonal selection (facilitated usually by the use of a selectable marker sequence in the vector) to select for stable transformants. Such stable transformants are then transferred to a mammal for therapeutic benefit therein.

The polypeptide of the invention can also be provided to the epithelial tubular cells by transfecting into a population of other cells a vector comprising the isolated polynucleotide encoding the polypeptide according to the invention, whereby the polypeptide is expressed in and secreted from said other cells. The population of other cells so transfected is then transferred to a site in the mammal where the polypeptide so secreted contacts renal tubular cells and prevents or treat a renal injury. Expression and secretion of the polypeptide from the other cells then has benefit on the renal tubular cells. It is not necessary that the DNA encoding the polypeptide be stably integrated into the cells. The polypeptide can be expressed and secreted from non-integrated or from integrated DNA in a cell.

Within the cells, the polynucleotide is expressed such that the cells express and secrete the polypeptide. Successful expression of the polynucleotide can be assessed using standard molecular biological techniques (e.g., Northern hybridization, Western blotting, immunoprecipitation, enzyme immunoassay, etc.). Reagents for detecting the expression of polynucleotides and the secretion of polypeptides from transfected cells are known in the art (see also examples herein below).

The polypeptide of the invention produced by recombinant techniques can be purified so that the polypeptide is substantially pure when administered to a subject. The term "substantially pure" refers to a compound, e.g., a protein or polypeptide, which has been separated from components, which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., by column chromatography, gel electrophoresis or HPLC analysis. A polypeptide is also substantially pure when it is essentially free of naturally associated components or when it is separated from the native contaminants, which accompany it in its natural state.

Pharmaceutical Compositions and Administration Routes

The present invention provides uses of pharmaceutical compositions comprising as an active agent a polypeptide capable of activating a gp130 signaling pathway. The present invention further provides uses of pharmaceutical compositions comprising as an active agent a polynucleotide encoding the polypeptide of the invention, expression vector comprising the polynucleotide or cells transfected with the expression vector and a pharmaceutically acceptable carrier. The pharmaceutical compositions of the invention are useful for the prevention or treatment of renal failure.

The present invention includes pharmaceutically acceptable salts of the polypeptides. Pharmaceutically acceptable salts include those formed with free amino groups such as those derived from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, oxalic, pamoic, pantothenic, phosphoric, succinic, sulfuric, tartaric, p-toluenesulfonic acid, and the like, and those formed with free carboxyl groups such as those derived from aluminum, ammonium, calcium, copper, ferric, ferrous, lithium, magnesium, manganic salts, manganous, potassium, sodium, zinc, primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active agent is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The compositions can take the form of solutions, suspensions, emulsions, tablets, pills, capsules, powders, suppositories, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the active agent of the invention, preferably in a substantially purified form, together with a suitable amount of carrier so as to provide the form for proper administration to the subject.

The amount of a polypeptide of the invention or an isolated polynucleotide encoding the polypeptide or an expression vector comprising the isolated polynucleotide encoding said polypeptide or cells expressing the polypeptide, which will be effective in the prevention or treatment of a renal injury or failure will depend on the nature of the renal injury, and can be determined by standard clinical techniques. For example, in vitro assays can optionally be employed to help identifying optimal dosage ranges. Alternatively or additionally, in vivo assays with animal models of renal failure can be performed to determine optimal dosage ranges (see examples herein below). The precise dose to be employed in the formulation will also depend on the route of administration, and the seriousness of the renal injury, and should be decided according to the judgment of the practitioner and each patient's circumstances. Effective doses may be extrapolated from dose-response curves derived from in vitro or animal model test bioassays or systems.

A composition comprising a source of a polypeptide of the invention (i.e., a polypeptide capable of activating a gp130 signaling pathway, or an isolated polynucleotide encoding the polypeptide, or an expression vector comprising the isolated polynucleotide encoding said polypeptide, or cells expressing the polypeptide, as described herein above) can be introduced into the systemic circulation, which will distribute the source of the polypeptide to the renal tissue. Alternatively, a composition containing a source of the polypeptide can be applied locally to the renal tissue (e.g., injected or as a bolus within the tissue).

Methods of introduction of a pharmaceutical composition comprising a source of a polypeptide of the invention include, but are not limited to, topical, intradermal, intramuscular, intraperitoneal, intravenous, subcutaneous, intranasal, epidural, and oral routes. The compounds can be administered by any convenient route, for example by infusion or bolus injection, by absorption through epithelial linings (e.g., oral mucosa, rectal and intestinal mucosa, etc.), and can be administered together with other therapeutically active agents. The administration can be localized, but it may be systemic.

It may be desirable to administer the pharmaceutical composition of the invention locally to the renal tissue in need of treatment; this can be achieved by, for example, and not by way of limitation, local infusion during surgery, topical application, e.g., in conjunction with a wound dressing after surgery, by injection, by means of a catheter, or by means of an implant, said implant being of a porous, non-porous, or gelatinous material. According to some embodiments, administration can be by direct injection e.g., via a syringe, at the site of a renal injury or by intravenous infusion.

According to some embodiments, a source of a polypeptide of the invention can be applied to the skin. The carrier can be in the form of, for example, and not by way of limitation, an ointment, cream, gel, paste, foam, aerosol, suppository, pad or gelled stick.

For directed internal applications, the pharmaceutical composition can be in the form of tablets or capsules, which can contain any of the following ingredients or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to the components listed above, a liquid carrier such as a fatty oil. In addition, dosage unit forms can contain various other materials which modify the physical form of the dosage unit, for example, coatings of sugar, shellac, or other enteric agents.

A polypeptide of the invention can be delivered in a controlled release system. In one embodiment, an infusion pump can be used to administer the polypeptide. Alternatively, the polypeptide of the invention can be administered in combination with a biodegradable, biocompatible polymeric implant, which releases the polypeptide over a controlled period of time at the renal tissue. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.).

Uses of the Compositions

The present invention provides a method for preventing or treating renal failure in a subject. The methods comprise administering to a subject in need thereof a pharmaceutical composition comprising as an active agent a therapeutically effective amount of a source of a polypeptide of the invention and a pharmaceutically acceptable carrier. The source of a polypeptide according to the present invention refers to a polypeptide capable of activating a gp130 signaling pathway; an isolated polynucleotide encoding the polypeptide of the invention; an expression vector comprising the isolated polynucleotide encoding the polypeptide of the invention; and a host cell transfected with an expression vector comprising an isolated polynucleotide encoding the polypeptide of the invention.

The terms "treating", "treat" or "treatment" as used herein include preventative (e.g., prophylactic), palliative and curative treatment. Thus, the methods of the present invention are useful for improving renal function in a subject in, or at risk of, renal failure. According to one embodiment, the subject is a mammal. According to another embodiment, the mammal is human.

By "therapeutically effective amount" is meant an amount effective to treat or prevent renal injury or failure, without undue adverse physiological effects or side effects. According to some embodiments of the present invention, renal failure to be treated is acute renal failure (ARF). According to additional embodiments, renal failure to be treated is chronic renal failure.

Acute renal failure (ARF) is a severe and often imminently life-threatening condition. There are many mechanisms that are known to be responsible for the pathogenesis of ARF. These include occlusions of the renal arteries, glomerular disease (glomerulonephritis, for one), infection (sepsis), disseminated intravascular coagulation (usually with cortical necrosis of the kidney), obstruction of urine flow due to tumors or other obstruction, acute tubular nephritis (ischemic or toxic), and others.

According to the present invention, acute renal failure includes, but is not limited to, acute renal failure arising from use or exposure to a pharmaceutical, diagnostic, or toxic agent selected from the group consisting of antibiotics including, but not limited to, aminoglycosides, antifungal agents including, but not limited to, amphotericin B, metals including, but not limited to, mercuric chloride, organic solvents, carbon tetrachloride, radiocontrast agents, imaging agents, and chemotherapeutic agents such as cis-platin.

According to the present invention, acute renal failure further includes, but is not limited to, acute renal failure arising from a disease, disorder, or condition selected from the group consisting of myoglobinuric rhabdomyolysis, hemoglobinuria, atheroembolic disease, renal artery occlusion, vasculitis, hemolytic-uremic syndrome, thrombolytic thrombocytopenic purpura, Wegener's granulomatosis, systemic lupus erythematosus, Henoch-Schoenlein purpura, Goodpasture's syndrome, acute glomerulonephritis, acute hypersensitivity interstitial nephritis, hypercalcemia, urinary tract obstruction, acute uric acid nephropathy, pyelonephritis, papillary necrosis, hepatorenal syndrome, hypertension, bacterial sepsis, post-ischemia, systemic inflammatory shock, fungemia, acute viral disease, severe volume depletion, blood transfusion reactions, post-partum complications, burns, ischemia reperfusion, and surgical procedures.

It is to be appreciated that the methods of the present invention are particularly useful for preventing renal injury or failure during kidney transplantation. Thus, the source of the polypeptide of the invention can be administered to a donor, whether living or post-mortem, prior or simultaneously with surgical removal of the kidney. Alternatively or additionally, the source of the polypeptide of the invention can be administered to a recipient prior, simultaneously or after kidney transplantation.

Chronic renal failure includes, but is not limited to, chronic diabetic nephropathy, diabetic glomerulopathy, diabetic renal hypertrophy, hypertensive nephrosclerosis, hypertensive glomerulosclerosis, renal dysplasia, glomerular hypertrophy, tubular hypertrophy, glomerulosclerosis and tubulointerstitial sclerosis.

Thus, the methods of the present invention provide cure or prophylactic treatment for acute or renal failure.

The source of the polypeptide of the present invention can be administered alone or in conjunction with other compounds such as, for example, erythropoietin (EPO), or with other therapeutic modalities.

EXAMPLES

Reagents

All chemicals were purchased from Sigma-Aldrich Chemicals (USA), unless otherwise stated. Recombinant human IL-6 was from PeproTech Inc. (Rocky Hill, N.J., USA). Sn(IV) Mesoporphyrin IX dichloride (SnMP) was purchased from Frontier Scientific Inc. (Logan Utah, USA).

Recombinant Hyper-IL-6 Protein

Hyper-IL-6 (HIL-6) is a protein complex consisting of human IL-6 covalently attached by a flexible peptide linker to the soluble IL-6R (sIL-6R) as defined by European Patent EP-B1 0 888 384. Recombinant Hyper-IL-6 protein was isolated from culture supernatants of genetically engineered Chinese Hamster Ovary (CHO) cells carrying a Hyper-IL-6 gene cassette (see, Fischer, M., et al., Nat. Biotechnol. 15: 142-145, 1997, the content of which is incorporated by reference as if fully set forth herein). Hyper-IL-6 was purified as previously described (Fischer, M., et al., ibid). Hyper-IL-6 (HIL-6) was stored at −80° C. A fresh aliquot was used for each experiment.

Animals

Male BALB/c and C57BL/6 mice (body weight 18-23 grams) were purchased from Harlan Laboratories Ltd., Jerusalem, and maintained in an animal facility at a temperature of ~23° C. in a 12-hour light-dark cycle under SPF conditions as assessed by regular microbiological screening. The mice received commercial rodent chow and water ad libitum and were acclimated for at least 4 days prior to use. Experimental procedures were performed according to the Institutional Animal Care and Use Committee approved animal treatment protocol (license number OPRR-A01-5011).

$HgCl_2$-Induced ARF

Acute Renal Failure (ARF) was induced by intra peritoneal (i.p) injection of $HgCl_2$ (6-8 mg/kg; Sigma-Aldrich Chemicals USA) dissolved in water as previously described (Nava, M., et al. Amer. J. Physiol. Renal Physiol. 279: F910-918, 2000). Mice were treated by intravenous injection of Hyper-IL-6 (8 µg), IL-6 (20 µg), or normal saline (carrier) in a volume of 150 µl, four hours prior to administration of $HgCl_2$. In indicated experiments, the mice were treated with an additional dosage of Hyper-IL-6 (4 µg) five hours following the administration of $HgCl_2$. The administration of a second dose of Hyper-IL-6 was shown in later experiments to be unnecessary for the protective effect.

Glycerol-Induced ARF and Inhibition of Heme Oxygenase Activity

BALB/c mice were anesthetized with Isoflurane® and injected with a solution of 50% glycerol in water, at a total dose of 8 ml/kg body weight, one-half dose injected into the anterior thigh muscle of each hind leg. Tin Mesoprotoporphyrin IX dichloride (SnMP), a specific inhibitor of heme oxygenase, was dissolved in one-third of the final volume with 0.1 N NaOH, adjusted to pH 8.0 with 0.1 N HCl and made up to a concentration of 3 mg/ml with normal saline, was administered at a dose of 20 µmol/kg body weight at 1.5 hours before, and 5 and 20 hours following administration of glycerol. Mice in parallel groups of the same experiment that were not administered SnMP received an equal volume of normal saline (i.p.) at the same time points.

Plasmid DNA Constructs

Expression plasmid DNAs, phAAT-IL6 and phAAT-HIL6, encoding human IL-6 and Hyper-IL-6, respectively, were constructed by ligation of a Hind III (filled)-Not I restriction fragments encoding human IL-6 and HIL-6 cDNAs, respectively, into the Sma I-Not I sites of pCI (Promega, Madison, Wis., USA), The CMV promoter was removed by digestion with Bgl II and Hind III, filled in at the Hind III site and replaced with a Bgl II-Not I (filled) DNA fragment containing the human $\alpha_1$-antitrypsin promoter (kindly provided by Dr. Katherine Ponder, University of Washington, St. Louis, Mo., USA). For in vivo administration by high pressure tail vein injection, plasmid DNAs were purified using a Qiagen Endotoxin-Free plasmid Maxi kit (Qiagen, Germany).

In Vivo DNA Transfection

In indicated experiments, animals were treated by hydrodynamics based in vivo plasmid DNA transfection (Liu, F., et al., 1999, Gene Ther. 6: 1258-1266, the content of which is incorporated by reference is fully set forth herein) with either phAAT-IL6 (10 µg), phAAT-HIL6 (2.5 µg), or a control plasmid, pGEM-7 (20 µg). All plasmid DNA solutions for injection were prepared in endotoxin tested normal saline and normalized with control plasmid DNA (pGEM-7) to 20 µg DNA in a final volume of 1.8 ml. Serum IL-6 and HIL-6 levels two days following hydrodynamics based in vivo transfection of plasmids phAAT-IL-6 and phAAT-HIL6 were approximately 50 ng/ml and 5 ng/ml, respectively, as determined by human IL-6 ELISA.

Determination of Blood Urea Nitrogen

Blood samples were obtained by tail vein bleeding at the indicated time periods after the induction of ARF. Blood urea nitrogen levels (BUN) were determined in heparinized serum using the Reflotron® system and Urea test strips (Roche Diagnostics GmbH, Mannheim, Germany).

Histological Analysis

Kidneys were surgically removed 24 to 48 hours after $HgCl_2$ administration. Renal tissue samples were fixed in 4% buffered formaldehyde, followed by 80% ethanol and embedded in paraffin blocks. Tissue sections of 2-4 micron thickness were stained with Hematoxylin-Eosin (H&E).

Western Blot Analysis

Protein extracts for analysis of pSTAT3, FLIP, Bcl-2, Bcl-xL were prepared from tissue samples ~100 mg) by homogenization in 1 ml whole cell lysis buffer (1% NP-40, 1 mM Tris pH 7.8, 150 mM NaCl, 40 mM EDTA, 10 mM Na-Pyrophosphate, 10 mM NaF, 1 mM PMSF, 4 mM Orthovanadate, Pepstatin A 1 ug/ml, Leupeptin 2 ug/ml). Protein extracts for analysis of IL-6R, were prepared by homogenization in m-PER buffer (Pierce) according to the manufacturer's instructions. Protein samples (50 µg) were separated by polyacrylamide gel electrophoresis and subjected to Western blot analysis. For analysis of murine IL-6R, Western blots were probed with goat anti-mouse IL-6R antibodies (R&D cat. No. AF1830) followed by rabbit anti-goat antibody (Zymed) and anti-rabbit HRP polymer (DAKO), and developed using the ECL-Plus Western blotting Detection System (Amersham). For analysis of pSTAT3 and STAT3, Western blots were probed with monoclonal anti-phosphorylated STAT3 (sc-8059) and monoclonal anti-STAT3 (sc-8019) (Santa Cruz), respectively. For analysis of FLIP, Bcl-2 and Bcl-xL, western blots were probed with a mouse monoclonal anti-human FLIP (sc-5276), a mouse monoclonal anti-human Bcl-2 (sc-7382) and a mouse monoclonal anti-human Bcl-xL (sc-8392) (Santa Cruz), respectively. As a loading control, the blots were stripped with 0.1 M glycine pH 2.8 and re-probed with a monoclonal anti-β-actin antibody, clone AC-74 (Sigma) and developed with anti-mouse HRP Envision kit (DAKO).

RNA Extraction and RT-PCR Analysis

RNA samples were prepared from approximately 100 mg snap-frozen tissue by homogenization in Trizol Reagent (Invitrogen) according to the manufactures instructions using a Polytron high-speed homogenizer and followed by treatment with DNA-free DNAse (Abion). Total cellular RNA samples (0.5 μg) were subjected to RT-PCR using Reverse-iT™ one-step RT-PCR kit (Abgene). The primer sequences used were as follows:

```
IL-6R (sense)
5'-AAGGAGTTCACGGTGTTGCT-3'        SEQ ID NO: 1
and

IL6R (anti-sense)
5'-TCGTACTGATCCTCGTGGTT-3';       SEQ ID NO: 2

β-actin (sense)
5'-AAGGTGACAGCATTGCTTCT-3'        SEQ ID NO: 3
and

β-actin (anti-sense)
5'-GGCTGCCTCAACACCTCA-3';         SEQ ID NO: 4

Bcl-xL (sense)
5'-GGTGAGTCGGATTGCAAGTT-3'        SEQ ID NO: 5
and

Bcl-xL (anti-sense)
5'-GAGGTGAGTGGACGGTCAGT-3';       SEQ ID NO: 6

SOCS3 (sense)
5'-TCAGTACCAGCGGAATCTTC-3'        SEQ ID NO: 7
and

SOCS3 (anti-sense)
5'-TACTGATCCAGGAATCTCCCGA-3';     SEQ ID NO: 8

HO-1 (sense)
5'-ATACAACCAGTGAGTGGAGC-3'        SEQ ID NO: 9
and

HO-1 (anti-sense)
5'-GTACAAGGAAGCCATCACCA-3';       SEQ ID NO: 10

Ref-1 (sense)
5'-CTGTACGAGGACCCTCCAGA-3'        SEQ ID NO: 11
and

Ref-1 (anti-sense)
5'-TCTTTGTCTGACGGAGCTGA-3';       SEQ ID NO: 12 gp130 (sense)
5'-CATGCTTTCAGGCTTTCCTC-3'        SEQ ID NO: 13
and gp130 (anti-sense)
5'-TCTCTGCTTCCACCCAGACT-3'.       SEQ ID NO: 14
```

Statistical Analysis

Mortality data were compared using Kaplan-Meier Survival Procedure and the Log Rank (Mantel-Cox) Test to compare equality of survival distributions with $P \leq 0.05$ considered statistically significant. All other comparisons were subjected to Student t-test with $P \leq 0.05$ considered statistically significant.

Example 1

Serum IL-6 Protein and Local STAT3 Signaling Increase Following $HgCl_2$-Induced Renal Injury Administration of mercury-containing compounds such as mercuric chloride ($HgCl_2$) is a well established and widely utilized model for the study of nephrotoxin induced acute renal failure (ARF). Administration of a toxic dose of $HgCl_2$ to mice resulted in a rapid and substantial elevation of serum IL-6 protein levels that was observed within one hour of administration (FIG. 1A). A large variance in IL-6 levels was apparent at 10 hours post $HgCl_2$ administration and is most likely associated with the variable toxicity of the $HgCl_2$ in the mice, some of which recovered rapidly whereas others displayed severe morbidity. RT-PCR analysis for IL-6 mRNA (FIG. 1B) showed that IL-6 gene expression following $HgCl_2$ administration was strongly induced in the kidney, indicating that the rise in serum IL-6 levels is in part due to the local induction of IL-6 expression in the kidney. IL-6 mRNA is also induced in the liver, and moderately so in the spleen. Concurrently with the rise in IL-6 levels, a significant increase in pSTAT3 (Tyr705) levels and up-regulation of SOCS3 mRNA in the kidney, suggesting an induction of gp130 signaling following $HgCl_2$ induced injury (FIGS. 1C and 1D).

Example 2

The Absence of IL-6R in the Kidney Precludes an IL-6 Mediated Protective Response In models of organ failure such as acute hepatic failure, IL-6 has been shown to have pleiotropic effects, participating in both inflammatory processes and tissue protection, depending on the time of administration.

Figure 2B:
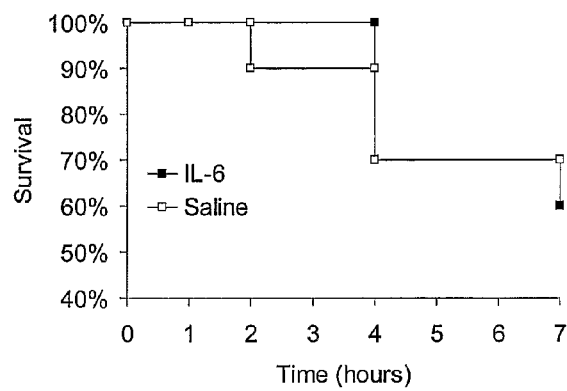

The possibility that pre-treatment with IL-6 can protect mice from $HgCl_2$-induced ARF was examined. Mice treated with IL-6 four hours prior to $HgCl_2$ administration displayed blood urea nitrogen (BUN) levels and mortality rate similar to those of control mice (FIGS. 2A and 2B). Prolonged exposure to IL-6 by hydrodynamics based in vivo transfection of an IL-6 expression plasmid (phAAT-IL6) also did not affect the levels of $HgCl_2$-induced ARF, indicating that the lack of an IL-6 induced effect was not due to insufficient bioavailability. Thus, IL-6 pretreatment neither reduced nor exacerbated $HgCl_2$-induced renal injury.

Figure 2C:
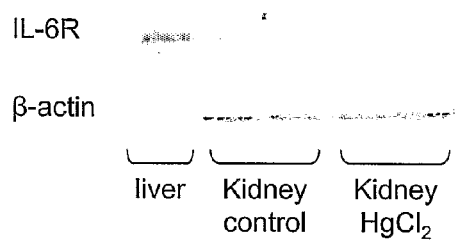
Figure 2D:
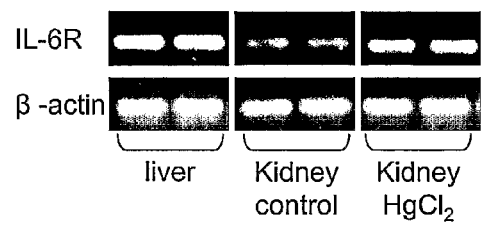

Responsiveness to IL-6 is dependent on the expression of either IL-6R on the target cell or on sIL-6R mediated trans-signaling. Because pretreatment of mice with IL-6 did not affect the outcome of $HgCl_2$ induced ARF, the expression of IL-6R in the renal parenchyma was examined. Western blot and RT-PCR analysis of tissue extracts from normal and $HgCl_2$ treated mice showed that IL-6R protein and mRNA are indeed expressed at very low levels in the normal mouse kidney in comparison to the liver which was used as a positive control (FIGS. 2C and 2D). Six hours after treatment with $HgCl_2$ a slight but clear increase in IL-6R mRNA was evident, however no change in the levels of IL-6R protein was apparent at this time (FIGS. 2C and 2D). Thus, the absence of IL-6R in the kidney precludes an IL-6 mediated protective response against $HgCl_2$ induced injury.

Example 3

Figure 3A:
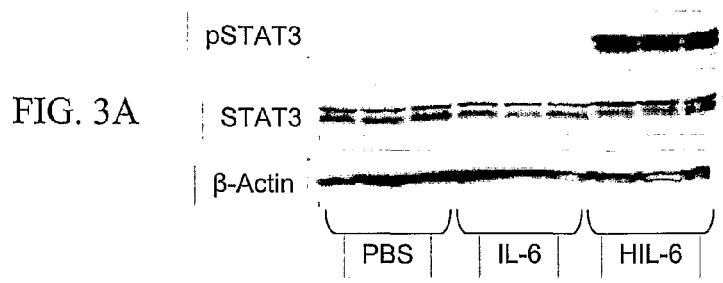
FIGS. 3A-E show the protecting effect of HIL-6 treatment from $HgCl_2$ induced ARF in mice.

Treatment with an IL-6/sIL-6R Fusion Protein Protects Mice from Acute Renal Failure Because of the lack of IL-6R in the kidney, the possibility that stimulation of gp130 signaling by an IL-6/sIL-6R complex would activate STAT3 and consequently protect the kidney from $HgCl_2$ induced ATN was studied. Mice were injected with the IL-6/sIL-6R fusion protein, Hyper-IL-6 (HIL-6) (Fischer, M., et al., ibid.) in order to directly stimulate gp130 in the kidney prior to $HgCl_2$ administration. HIL-6 is fully active on gp130-expressing cells and acts as a gp130 super-agonist both in vitro and in vivo. To determine whether HIL-6 is able to stimulate gp130 signaling in the mouse kidney the ability of HIL-6 to trigger STAT3 activation was analyzed. Injection of HIL-6 to mice led to a strong stimulation of STAT3 phosphorylation (FIG. 3A) in the kidney. Both α and β isoforms of STAT3 are expressed in the kidney, and both appear to be equally phosphorylated following exposure to HIL-6 (FIG. 3A). In contrast, IL-6 had little effect on STAT3 phosphorylation in the kidney, commensurate with the paucity of IL-6R expression (FIG. 3A). These results demonstrate the efficacy of HIL-6 in stimulating the gp130 signal transduction pathway in the kidney.

Figure 3B:
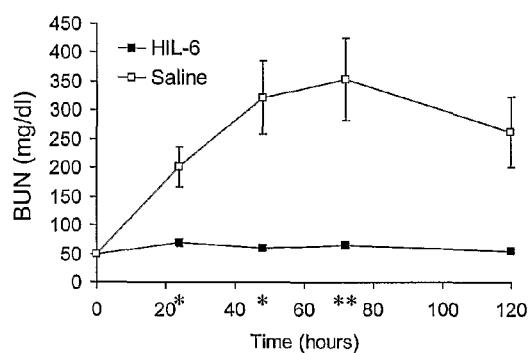
Figure 3C:
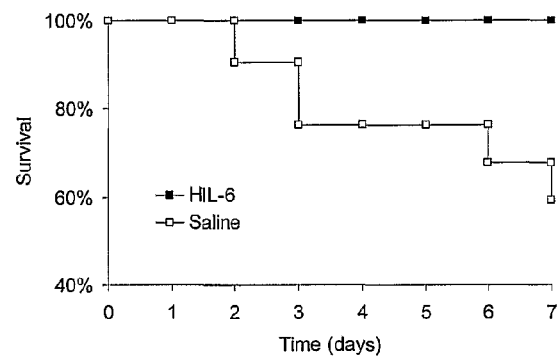
Figures 3D, 3E:
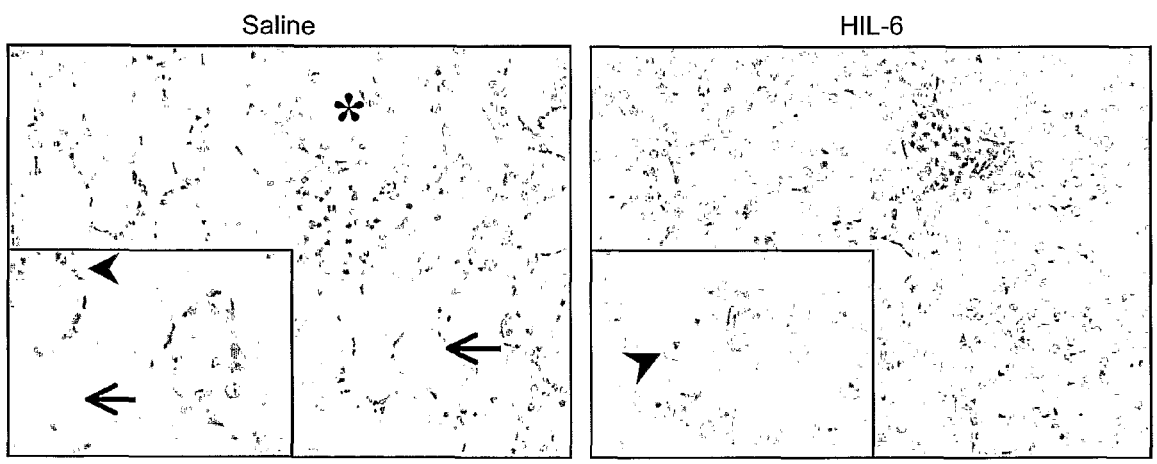

To assess the effect of HIL-6 on the development of ARF, mice were treated with HIL-6 protein four hours prior to administration of $HgCl_2$ and the development of renal injury was monitored. In contrast to the control group, mice treated with HIL-6 were dramatically resistant to $HgCl_2$ induced ARF, displaying only a marginal increase in blood urea levels (FIG. 3B). Strikingly, whereas control treated mice displayed significant mortality, mice treated with HIL-6 all survived (log rank test, P<0.007) (FIG. 3C). Histological examination of kidney samples from control mice taken 24 hours after induction of ATN showed necrosis of proximal tubules, intraluminal accumulation of proteinaceous material, dilated tubuli and congestion of peritubular capillaries showing margination of neutrophils (FIG. 3D). In contrast, the HIL-6 treated mice displayed only subtle tubular dilatation and occasional apoptotic epithelial cells (FIG. 3E).

Example 4

HIL-6 Induces Anti-Oxidant Factors in the Kidney

Figure 4A:
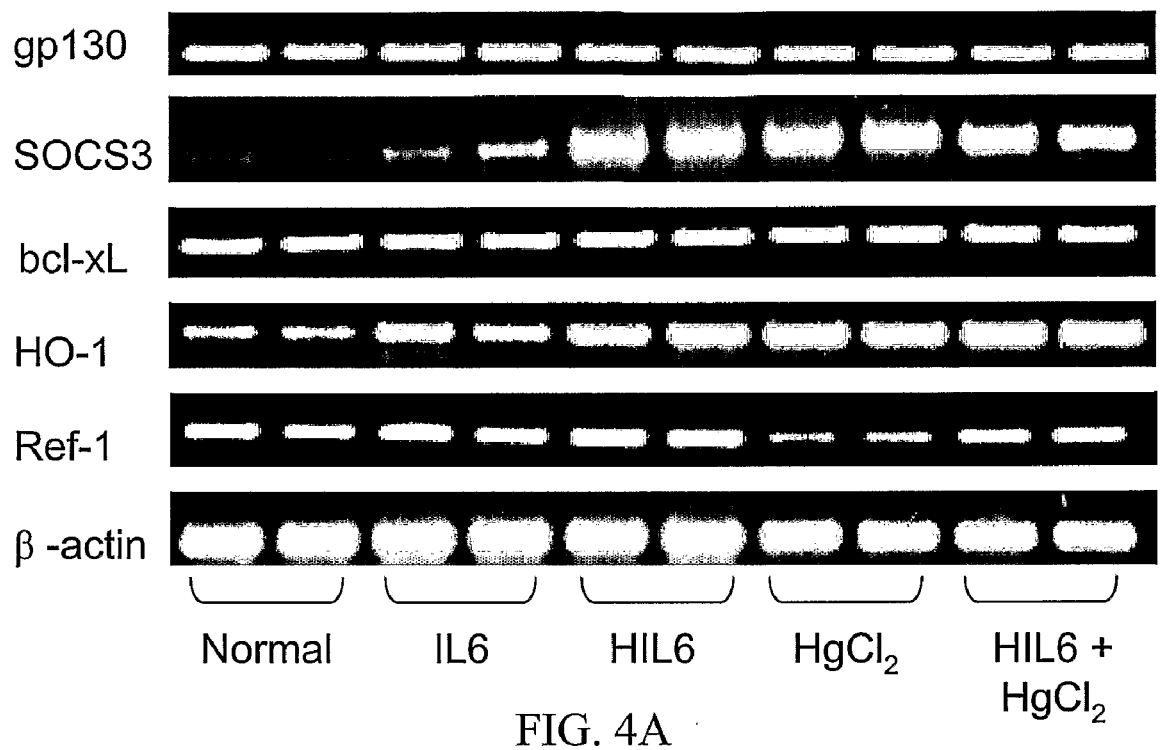
FIGS. 4A-B show the effect of HIL-6 and IL-6 on the expression of anti-apoptotic and oxidative stress response genes in normal and $HgCl_2$ treated mice.
Figure 4B:
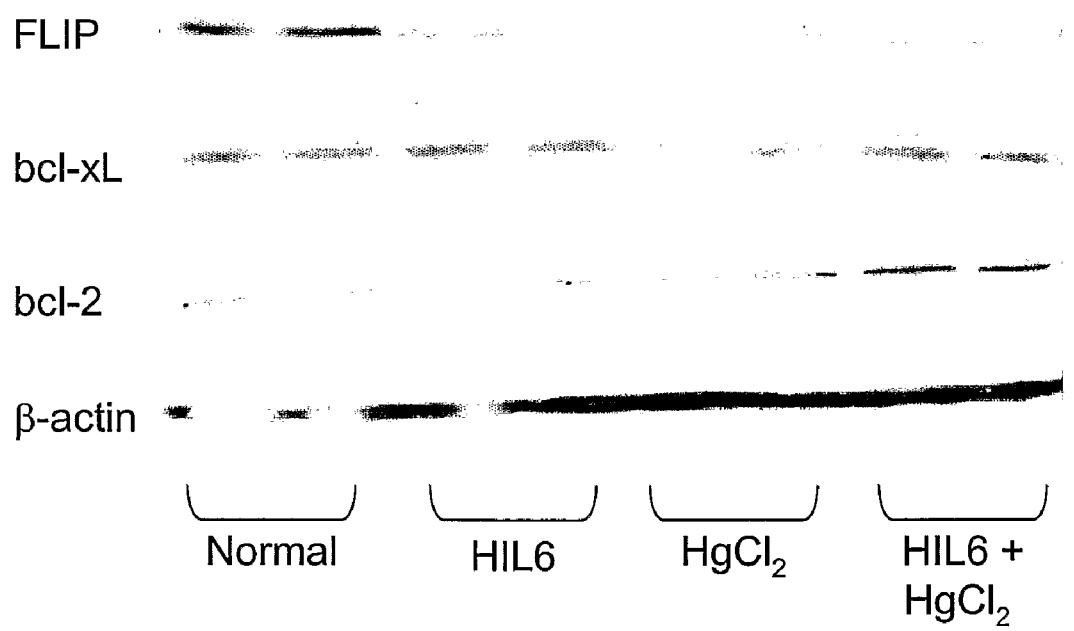

The mechanism of $HgCl_2$ induced ATN involves an increase in oxidative stress, leading to apoptosis and necrosis of the proximal tubular epithelial cells. In order to elucidate the mechanism by which gp130 signaling protects the kidney, the effect of HIL-6 treatment on the expression of anti-apoptotic and oxidative stress related factors was examined). RT-PCR analysis of kidney RNA revealed that gp130 mRNA was constitutively expressed in the kidney and was not affected by treatment with HIL-6, IL-6, or the induction of renal injury (FIG. 4A). Analysis of kidney RNA samples taken 4 hours after treatment with HIL-6 or IL-6 revealed that SOCS3 mRNA was strongly induced by HIL-6, but not by IL-6 (FIG. 4A), again confirming both the presence of gp130 protein and the relative absence of IL-6R in the kidney. SOCS3 mRNA expression was again observed to be strongly up-regulated shortly after $HgCl_2$ administration, but was not enhanced further by HIL-6 treatment prior to $HgCl_2$ administration (FIG. 4A). In contrast, no substantial changes were observed in the mRNA or protein levels of anti-apoptotic factors Bcl-2, Bcl-xL, or FLIP following any of the treatments tested (FIGS. 4A and 4B). Thus, the protective effect of HIL-6 treatment does not appear to be mediated through the immediate up-regulation of these anti-apoptotic factors in the kidney.

The nephrotoxicity of mercury is largely attributed to renal generation of reactive oxygen species (ROS) such as hydrogen peroxide. In response to oxidant injury mammalian cells are known to up-regulate a number of redox responsive genes including heme oxygenase (HO-1) and the multifunctional nuclear protein, apurinic endonuclease/redox effector factor (Ref-1). Consistent with these findings, a strong induction of HO-1 mRNA following $HgCl_2$ administration was observed (FIG. 4A). HO-1 expression was also strongly up-regulated by HIL-6 treatment, and even more so in mice administered HIL-6 prior to $HgCl_2$ treatment (FIG. 4A). Contrary to our expectations, Ref-1 mRNA levels in the kidney were markedly reduced following $HgCl_2$ administration (FIG. 4A). However, treatment with HIL-6 substantially increased Ref-1 mRNA expression, and treatment with HIL-6 prior to $HgCl_2$ administration maintained Ref-1 mRNA at normal levels (FIG. 4A). These results suggest that Ref-1 maybe an important factor in HIL-6 induced protection to $HgCl_2$ induced ATN.

To determine whether the induction of HO-1 contributed to the protection observed after HIL-6 administration, the effect of HIL-6 in the presence of the specific competitive inhibitor of HO-1 activity, tin mesoprotoporphyrin (SnMP) was studied. However, administration of SnMP did not prevent the HIL-6 generated resistance to $HgCl_2$ induced ARF (BUN at 24 hours=103±43, 47±10 and 44±10 mg/dl (n=8) in Saline treated, HIL-6 treated and HIL-6+SnMP treated mice, respectively, P<0.003 for HIL-6 vs saline, and P=0.54 for HIL-6 vs HIL-6+SnMP).

Next the possibility that HIL-6 treatment would prevent glycerol-induced abrupt rhabdomyolysis, where HO-1 activity is essential to injury resistance, was studied. Glycerol-induced ARF is caused by complex pathophysiological processes involving toxic proximal tubular cell damage, vasoconstriction with hypoxic tubular damage, inflammatory response, and tubular obstruction. A single injection of HIL-6 protein prior to glycerol-induced ARF resulted in only a moderate protective effect of inconsistent statistical significance (Table 1) suggesting that a higher or extended dosing regimen of HIL-6 may be required in order to generate resistance to glycerol induced injury.

TABLE 1

The effect of HIL-6 Protein on Renal Function Following Glycerol Induced ARF

| Exp. No. | BUN (mg/dl), 24 h | | BUN (mg/dl), 48 h | |
|---|---|---|---|---|
| | Saline (n) | HIL-6 (n) | Saline (n) | HIL-6 (n) |
| 1 | 366 ± 93 (5) | 185 ± 46 (6)[a] | 381 ± 195 (5) | 200 ± 51 (6)[b] |
| 2 | 303 ± 104 (5) | 236 ± 74 (5)[c] | 316 ± 127 (5) | 188 ± 45 (5)[b] |
| 3 | 335 ± 99 (7) | 299 ± 27 (6)[c] | 377 ± 160 (7) | 273 ± 44 (6)[c] |

Data shown are mean values ± standard deviation.
[a] P < 0.003 vs control;
[b] P < 0.05 vs control;
[c] P = ns vs control.

Figure 5:
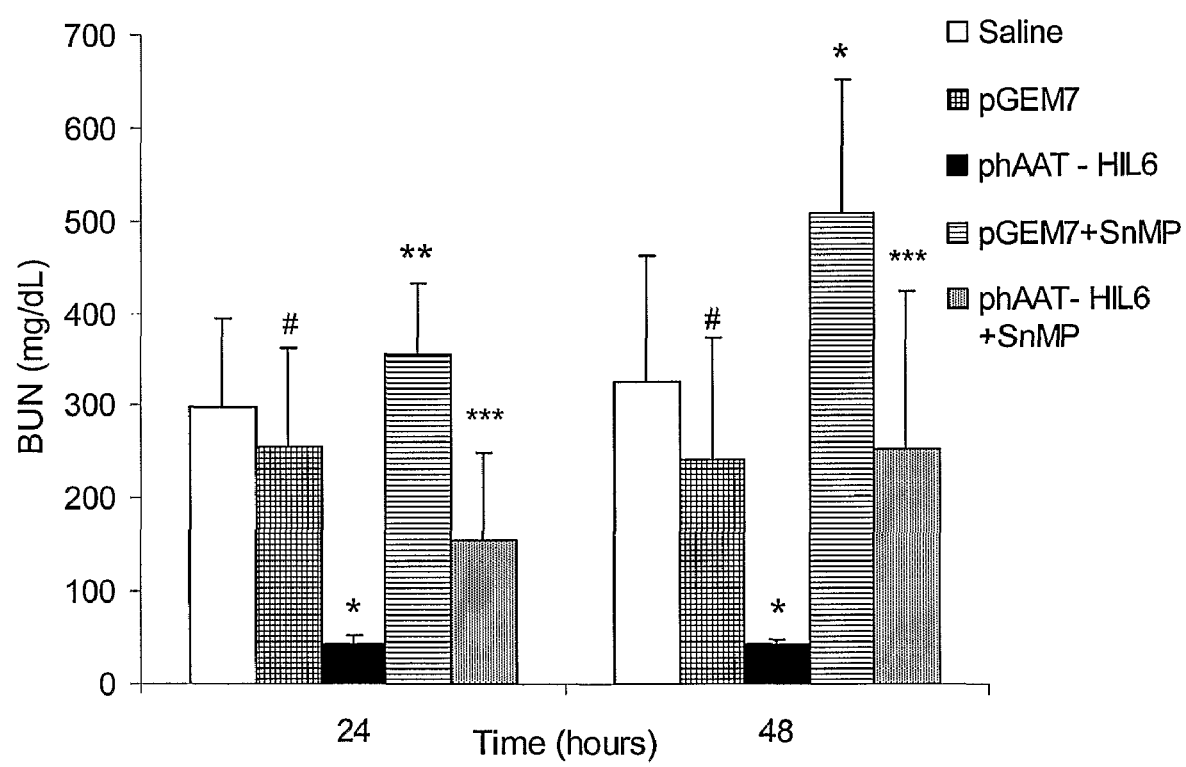
FIG. 5 shows the protecting effect of HIL-6 from glycerol induced ARF in mice, which effect is blocked by inhibitors of HO-1 activity. Renal function as measured by BUN levels in mice treated with 50% glycerol (i.m.) was evaluated in mice treated by hydrodynamics based in vivo DNA transfection with an HIL-6 expression plasmid (phAAT-HIL6) 48 hours prior to induction of ARF (solid bars), in control plasmid DNA (pGEM-7) transfected (cross-hatched bars) mice, in normal saline treated mice (open bars), in control plasmid transfected mice treated with the HO-1 inhibitor, SnMP (horizontal-line bars), and in phAAT-HIL6 transfected mice treated with SnMP (speckled bars). Results are expressed as mean±SD. *P<0.001 vs pGEM-7, P<0.01 vs pGEM-7, *P<0.001 vs phAAT-HIL-6, #P=ns vs Saline.

In order to extend the HIL-6 dosing, mice were transfected with the HIL-6 expression plasmid, phAAT-HIL6, two days prior to glycerol injection. As shown in FIG. 5, mice transfected with phAAT-HIL6 were dramatically resistant to glycerol induced ARF, but inhibition of HO-1 activity by SnMP significantly blocked the protective effect of HIL-6, leading to ARF levels similar to that of the plasmid DNA control group 48 hours post injury (FIG. 5). SnMP treatment of control plasmid transfected mice also strongly exacerbated the renal injury, although SnMP per se was not nephrotoxic. This indicates that the induction of HO-1 expression in the kidney is essential to HIL-6 generated resistance to glycerol-induced ARF, but not to $HgCl_2$ induced ARF. Without wishing to be bound to any mechanism of action, these results may indicate that HIL-6 induced protection to $HgCl_2$ induced ARF is largely mediated by mechanisms that ameliorate oxidative stress.

CONCLUSIONS

Pre-treatment of the mice with IL-6 did not prevent either the onset of ARF caused by $HgCl_2$, or related mortality. The present findings are similar to those of Homsi et. al. who have reported that IL-6 pre-treatment failed to prevent the onset of glycerol-induced ARF (Homsi, E., et al. 2002, Nephron 92: 192-199). As an explanation of this observation, the present study demonstrates a notable paucity of IL-6R expression in normal kidney, which precludes a physiological influence of IL-6 directly on tubular epithelial cells. Nevertheless, a significant increase in STATS activation and up-regulation of SOCS3 mRNA was observed, suggesting the presence of significant gp130 signaling following renal injury and that activation of the gp130 signaling pathway is an inherent physiological response to renal injury. Indeed, a strong induction of mRNAs and proteins of various gp130 activating cytokines, including IL-6, IL-11 and leukemia inhibitory factor (LIF) has also been observed following ischemic-reperfusion induced renal injury (Lemay, S., et al., 2000, Transplantation 69: 959-963). Notably, expression of both LIF and LIFR was observed in the proximal tubular cells of the outer medulla, where LIF or LIFR are not normally expressed.

The present study provides the first direct demonstration that activation of gp130 signaling in the kidney ameliorates ARF. The similar findings observed in two independent and dissimilar models of ARF suggest that induction of a broad protective response to various forms of renal injury is a primary function of gp130 signaling in the renal parenchyma.

Oxidative stress is a cardinal element in the mechanism of $HgCl_2$ induced renal injury, and leads to a strong up-regulation of the redox sensitive genes including HO-1. Administration of HIL-6 also strongly induced HO-1 gene expression, which was up-regulated even further by the sequential administration of HIL-6 and $HgCl_2$. Induction of HO-1 is an important element in the protective response to glycerol-induced renal injury, but HO-1 induction per se is unable to provide protection against $HgCl_2$ induced injury. In concurrence with these observations, the present study indicates that inhibition of HO-1 activity significantly blocked the protective effect of HIL-6 to glycerol-induced injury, but not to that of $HgCl_2$ induced renal injury. It is therefore suggested that gp130 signaling produces an overall protective response to various sources of renal injury via induction of multiple factors. Ref-1 appears to be one such factor.

Ref-1 is a nuclear protein which acts in a mutually exclusive fashion as both an endonuclease in the base excision repair pathway and as a reducing agent that facilitates the DNA-binding activities of many redox-sensitive transcription factors, including NF-κB. Ref-1 is up-regulated in response to stimuli that result in intracellular ROS generation, as well as to oxidative agents themselves, including hydrogen peroxide, and Ref-1 expression is regulated by STAT3. Induction of Ref-1 is associated with an increase in a cell's adaptive resistance to hydrogen peroxide, which is produced in copious amounts by renal epithelial cells in vitro and in vivo when exposed to $HgCl_2$. Overall, the present results indicate that gp130 mediated protection against renal injury is largely mediated by mechanisms that ameliorate oxidative stress. The involvement of anti-apoptotic factors at early times after either HIL-6 or $HgCl_2$ administration was not observed, yet the possibility that these or other anti-apoptotic factors play a role at later times in the development of ARF cannot at present be ruled out.

This study directly supports the conclusion that an HIL-6 based therapeutic strategy may be useful to protect the kidney from injury, and provide overall maintenance of renal function during stress.

It will be appreciated by persons skilled in the art that the present invention is not limited by what has been particularly shown and described herein above. Rather the scope of the invention is defined by the claims that follow.

The invention claimed is:

1. A method for treating acute renal failure in a subject which comprises administering to the subject a therapeutically effective amount of an active agent of (a) a complex comprising IL-6/soluble IL-6 receptor (sIL-6R) or a salt thereof, or (b) a complex comprising a biologically active fragment of IL-6 which comprises amino acids 29-212 of human IL-6 polypeptide, and a biologically active fragment of sIL-6R comprising amino acids 113-323 of sIL-6R, or salt thereof, thereby treating acute renal failure.

2. The method of claim 1, wherein the active agent is administered in a pharmaceutical composition that includes the agent and a pharmaceutically acceptable carrier.

3. The method of claim 1, wherein the route of administering the pharmaceutical composition is selected from the group consisting of topical, intradermal, intramuscular, intraperitoneal, intravenous, subcutaneous, intranasal, epidural, and oral administration routes.

4. The method of claim 3, wherein the route of administering is via intravenous administration.

5. The method of claim 1, wherein the acute renal failure arises from use or exposure to a pharmaceutical, diagnostic, or toxic agent selected from the group consisting of antibiotics, antifungal agents, radio-contrast agents, imaging agents, chemotherapeutic agents, metals, organic solvents, and carbon tetrachloride.

6. The method of claim 1, wherein the acute renal failure arises from a disease, disorder, or condition selected from the group consisting of myoglobinuric rhabdomyolysis, hemoglobinuria, atheroembolic disease, renal artery occlusion, vasculitis, hemolytic-uremic syndrome, thrombolytic thrombocytopenic purpura, Wegener's granulomatosis, systemic lupus erythematosus, Henoch-Schoenlein purpura, Goodpasture's syndrome, acute glomerulonephritis, acute hypersensitivity interstitial nephritis, hypercalcemia, urinary tract obstruction, acute uric acid nephropathy, pyelonephritis, papillary necrosis, hepatorenal syndrome, hypertension, bacterial sepsis, systemic inflammatory shock, fungemia, acute viral disease, severe volume depletion, burns, ischemia-reperfusion, post-partum complications, and surgical procedures.

7. The method of claim 1, wherein the active agent is Hyper-IL-6.

* * * * *